(12) United States Patent
He et al.

(10) Patent No.: US 6,573,734 B2
(45) Date of Patent: Jun. 3, 2003

(54) INTEGRATED THIN FILM LIQUID CONDUCTIVITY SENSOR

(75) Inventors: Dongming He, Chandler, AZ (US); Mark A. Shannon, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/850,719

(22) Filed: May 8, 2001

(65) Prior Publication Data

US 2002/0167322 A1 Nov. 14, 2002

(51) Int. Cl.[7] .............................................. G01R 27/08
(52) U.S. Cl. ......................................................... 324/696
(58) Field of Search ................................. 324/439, 441, 324/444, 691, 693, 696

(56) References Cited

U.S. PATENT DOCUMENTS

| | | | |
|---|---|---|---|
| 3,936,729 A | 2/1976 | Winslow, Jr. | 324/450 |
| 4,331,923 A | 5/1982 | Akers, Jr. | 324/449 |
| 4,359,687 A * | 11/1982 | Vinegar et al. | 324/366 |
| 4,365,200 A | 12/1982 | Goldsmith | 324/449 |
| 4,449,396 A | 5/1984 | Bzdula | 73/61.61 |
| 4,498,305 A | 2/1985 | Bzdula | 62/84 |
| 4,626,786 A | 12/1986 | Bodecker et al. | 324/449 |
| 4,656,427 A | 4/1987 | Dauphinee | 324/444 |
| 4,719,441 A | 1/1988 | Horn | 338/20 |
| 4,802,953 A | 2/1989 | Hoeksema et al. | 162/263 |
| 4,808,931 A | 2/1989 | Ling | 324/444 |
| 4,833,413 A | 5/1989 | Head | 324/449 |
| 5,005,399 A | 4/1991 | Holtzclaw et al. | 73/23.39 |
| 5,134,376 A | 7/1992 | Iwamoto | 324/447 |
| 5,287,060 A | 2/1994 | Reddy et al. | 324/439 |
| 5,483,164 A * | 1/1996 | Moss et al. | 324/425 |
| 5,519,323 A | 5/1996 | Kordas et al. | 324/444 |
| 5,543,717 A | 8/1996 | Kordas | 324/444 |
| 5,933,016 A | 8/1999 | Kauffman et al. | 324/698 |
| 5,945,830 A | 8/1999 | Magowan et al. | 324/438 |

OTHER PUBLICATIONS

Japanese Patent Abstract No. 08240574, published Sep. 17, 1996.
Japanese Patent Abstract No. 08240575, published Sep. 17, 1996.
Japanese Patent Abstract No. 43039 filed Nov. 15, 1991.
English translation of Ref. (3).

(List continued on next page.)

*Primary Examiner*—Safet Metjahic
*Assistant Examiner*—Etienne P LeRoux
(74) *Attorney, Agent, or Firm*—Greer, Burns & Crain, Ltd.

(57) ABSTRACT

A thin film integrated conductivity sensor is formed on a suitable surface for measuring the electrical conductivity of a liquid. The surface is preferably an insulator, but may be conducting, if the electrodes are on an insulating surface. A preferred embodiment insulates the electrodes by use of a dielectric layer that is deposited on top of a silicon wafer substrate. A sensor tip is integrated on the top surface of the substrate. In a preferred embodiment, the substrate is fabricated into a sensor shape with a small sharp tip at one end and an opposite larger end for accommodating electrode pads. The larger end might also be used for integration of measurement circuits or accommodating bonding pads. In a preferred embodiment, the tip also accommodates an integrated temperature sensor to enable local temperature measurements. The sensor is a thin-film resistor preferably enclosed within a layer of the sensor tip and having a serpentine shape to produce significant resistance (hundreds to thousands of Ohms) while consuming a small area of the sensor tip.

21 Claims, 3 Drawing Sheets

OTHER PUBLICATIONS

JPO Office Action of Oct. 29, 2002.

N. Kordas, Y. Manoli, W. Mokwa and M. Rospert, *A CMOS–compatible monolithic conductivity sensor with integrated electrodes*, Sensors and Actuators A, 43 (1994) pp. 31–37.

W. Olthuis, A. Volanschi, J.G. Bomer and P. Bergveld, *A new probe for measuring electrolytic conductance*, Sensors and Actuators B, 13–14 (1993), pp. 230–233.

W. Olthuis, W. Streekstra, P. Bergveld, *Theoretical and Experimental determination of cell constants of planar–interdigitated electrolyte conductivity sensors*, Sensors and Actuators B 24 25, (1995) pp. 252–256.

Dongming He and Mark A. Shannon, *Deep Reactive Ion Etched Liquid Conductivity Probes with Integrated Temperature Sensor*, Category 9 Microchemical Analysis Systems and Biomems, MEMS 2001–Unpublished.

* cited by examiner

INTEGRATED THIN FILM LIQUID CONDUCTIVITY SENSOR

STATEMENT OF GOVERNMENT INTEREST

This invention was made with government assistance under DARPA Contract DABT63-98-0053T-3. The government has certain rights in this invention.

FIELD OF THE INVENTION

This invention relates to a sensor for measuring the electrical conductivity of a liquid. More specifically, the present invention provides a conductivity sensor with an integrated temperature sensor for measuring ion concentrations in very small samples, including in vivo and in-situ chemical or biological fluid analysis.

BACKGROUND OF THE INVENTION

Conductivity of a liquid solution provides information about the solution. Measuring the conductivity of a solution by electrical means is a difficult problem, especially in small volumes. Electrons and ions accumulate at an electrode/liquid interface of an electrical sensor, creating a surface potential between the electrode and the solution that must be accounted for in determining conductivity.

Many devices might benefit from a conductivity sensor having accuracy in small liquid volumes. For example, development of a portable unit for purifying water in remote areas requires use of small sensors to detect the presence of salts, or other solutes, to measure effectiveness of the unit. Accurate small sensors might also be advantageously applied as part of a system to automatically determine rinse cycle end in a clothes washer, cycle end in a water softener, or a cycle end in a water purifier.

Commercially available conductivity probes have diameters greater than 1 cm, limiting their potential applications. Such a probe is accurate for sample volumes of more than 10 ml. Their size leads to a large time constant, requiring tens of seconds to reach equilibrium, thus yielding a slow response time. As probes become smaller, sample size and response times become smaller but surface effects and other problems become more important. Small probes also present fabrication problems unresolved by the conventional configuration of larger probes, i.e., the large probes do not scale down.

An accurate sensor must account for the variance of conductivity with temperature. In large probes, a separate temperature sensor can be used to measure the temperature and adjust the conductivity measure. Use of a separate temperature probe is inaccurate or impossible with a small probe in a small liquid volume, where the local temperature at the probe is influential.

In certain settings, the ambient temperature can be controlled such that it is known with a high degree of accuracy. However, conventionally sized and packaged conductivity probes are inaccurate for small sample volumes, even if the temperature is known to high accuracy. As the volume of liquid approaches the size of the sensor, large errors result in conductivity measurements, since the cell constant, $K_c$, changes, i.e., it is no longer a constant. $K_c$ is important since it is used to calibrate the sensor, in order to determine conductivity, and therefore ion concentration, from the electrical resistance.

SUMMARY OF THE INVENTION

The present invention provides a microscale thin film liquid conductivity sensor capable of sensing conductivity in very small volumes and which can be fabricated as part of an integrated circuit. A preferred embodiment includes an integrated temperature sensor.

The thin film sensor is formed on a suitable surface. The surface is preferably an insulator, but may be conducting, if the electrodes are on an insulating surface. A preferred embodiment insulates the electrodes by use of a dielectric layer that is deposited on top of a silicon wafer substrate. A sensor tip is integrated on the top surface of the substrate. The substrate is fabricated into a sensor shape with a small sharp tip at one end and an opposite end that can be larger to accommodate electrode measurement pads. The larger end might also be used for integration of measurement circuits or accommodating wire bonding pads. In a preferred embodiment, the tip also accommodates an integrated temperature sensor to enable local temperature measurements. The sensor is a thin-film resistor preferably enclosed within a layer of the sensor tip and having a serpentine shape to obtain a desired resistance in a smaller active area while consuming a small area of the sensor tip.

The sensor of the invention may be made very small and may be integrated with circuitry. An exemplary 100 $\mu$m sensor has been fabricated. Larger sensors of the invention can be made arbitrarily smaller than commercially available 1 cm diameter sensors. It is the structure of the invention which is important, however, allowing not only very small sensor sizes but also permitting integration of the sensor with integrated calculation circuits, etc. Artisans will appreciate the size advantages offered by the structure, while recognizing that size may be optimized to achieve desirable goals. For example, smaller sensors of the invention tending toward 100 $\mu$m and below are more difficult to fabricate, and more difficult to obtain an accurate measurement than a 500 $\mu$m sensor or 1 mm sensor of the invention. However, the smaller sensors obviously consume a smaller area of substrate. These competing design goals may be balanced to suit particular applications in using a sensor of the invention

DETAILED DESCRIPTION OF THE DRAWINGS

Figure 2D:
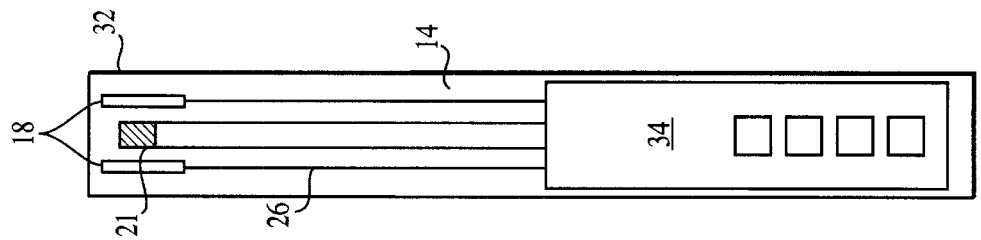
Figure 2C:
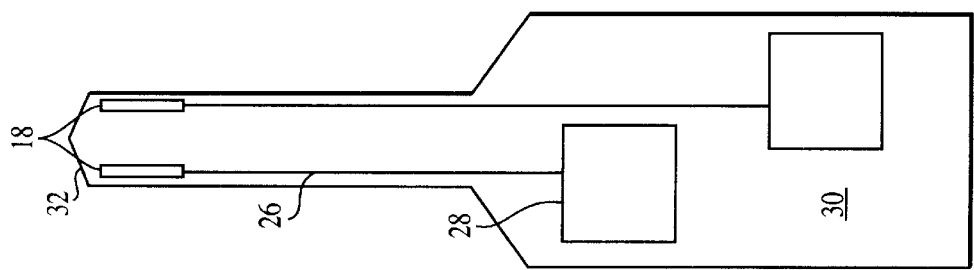
Figure 2B:
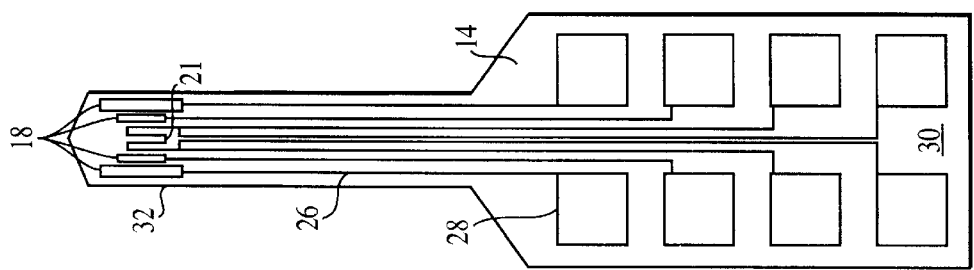
Figure 2A:
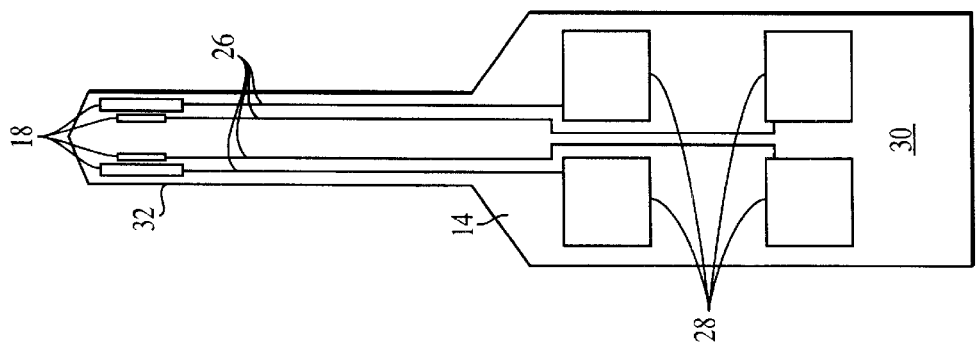
Figure 3:
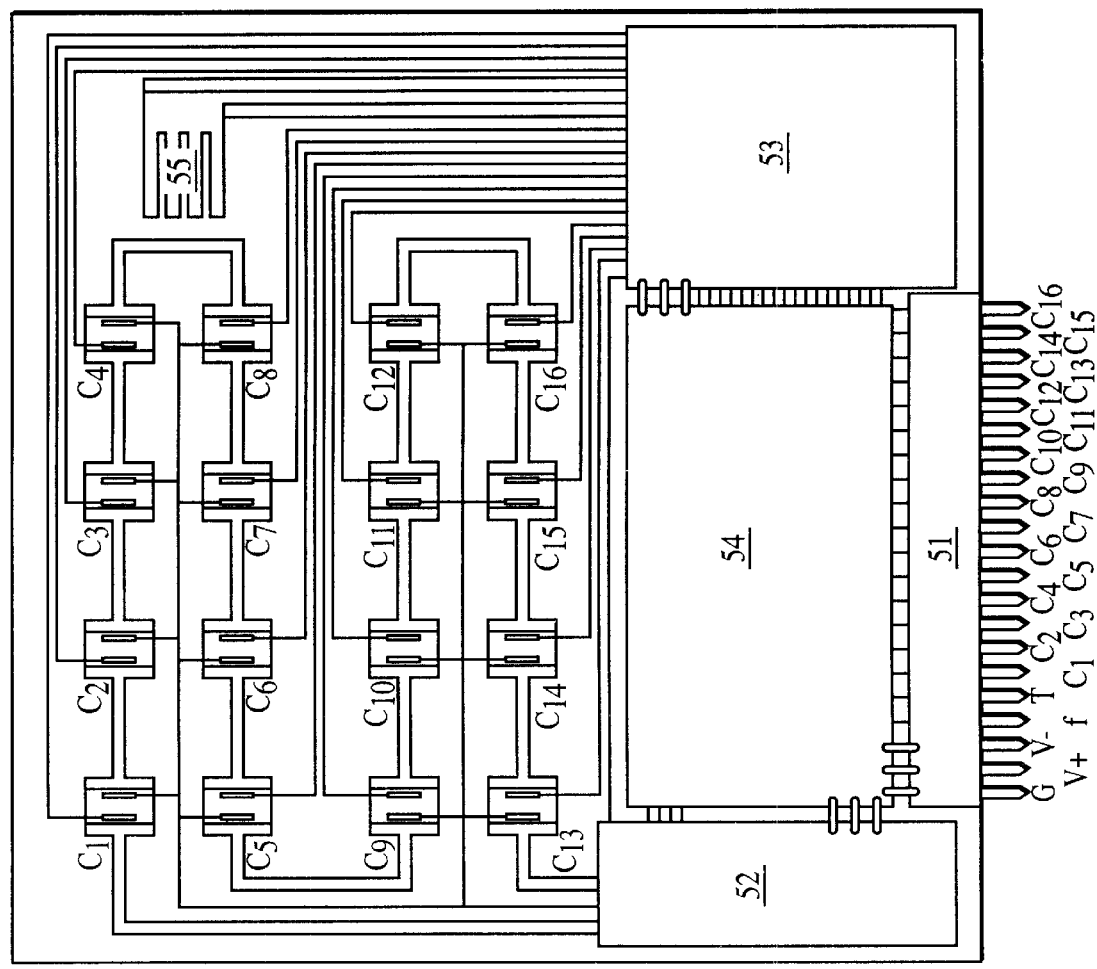

FIGS. 2a–2d are top views of four separate sensors of the invention. FIG. 2a illustrates a four-electrode sensor. FIG. 2b shows a four-electrode sensor including a four-wire temperature sensor. FIG. 2c shows a simple two-electrode sensor. FIG. 2d shows a two-electrode sensor including a two-wire temperature sensor with an integrated measurement circuit; and FIG. 3 is the top view of an integrated device including an array of sixteen four-electrode conductivity sensors C1–C16, combined with a four-wire temperature sensor, packaged with driving and measurement circuitry.

DETAILED DESCRIPTION OF THE INVENTION

Figure 1A:
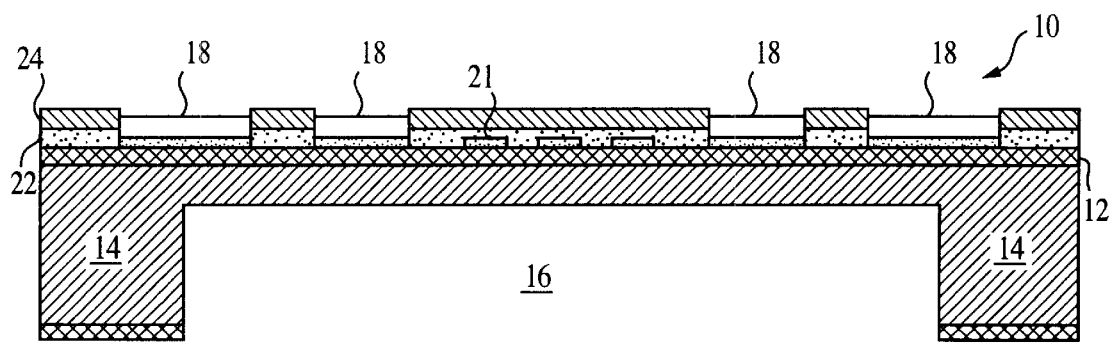
FIG. 1a is a cross-sectional view of the sensor tip of a preferred embodiment four-electrode sensor of the present invention including an integrated four-wire thin-film resistor and formed into a probe shape.

Referring now to FIG. 1a, a preferred embodiment four-electrode thin film sensor, generally designated 10, is shown. FIG. 1a is a cross section looking into the tip end of a sensor. The sensor 10 is formed on a dielectric layer of thermal oxide material 12, which insulates the sensor from a substrate such as a silicon wafer base 14. A silicon substrate provides great opportunity to integrate the sensor 10 with integrated circuits. However, virtually any material forms a suitable substrate, e.g., glass, ceramics, or metals if an insulating layer is placed on top. Generally, the sensor 10 simply requires an electrically insulating surface. A separate insulating layer may be omitted where the substrate itself is insulating. Accordingly, the sensor of the invention may be integrally formed with circuitry, including, for example, semiconductor circuitry.

Accuracy of measurement is improved by enhancing heat transfer between the sensor tip and a surrounding environment into which it is introduced so it can reach thermal equilibrium faster. However, optimal operation is obtained when heat transfer along the sensor by conduction to the packaging and the outside is minimized. That latter function is served by reducing the mass or cross-sectional area of the substrate beneath the sensor, as accomplished by the recess 16 in FIG. 1a and the T-structure of the substrate 14 in FIG. 1b. Lower substrate mass reduces the thermal mass of the sensor, lowering the time required to reach a thermal equilibrium, and improving the response time of the sensor 10. It is therefore advantageous to remove material from the back of substrate 14, forming cavities 16 to reduce the mass and to reduce the thermal conduction cross section along the sensor by etching, micromachining or any suitable technique. The thickness can be thinned to less than a micron in thickness, if desired, by growing a layer of silicon nitride and/or oxide on silicon, and then removing the silicon directly underneath the sensor, so that a membrane supports the sensor. Employing membranes as the sensor base reduces the thermal mass to the minimum.

A plurality of conductivity electrodes 18 is located on the sensor tip 10. Preferably the electrodes 18 are on opposite sides of the sensor tip, however, location is not critical as long as the electrodes 18 are parallel to each other and spread apart to allow conductance of an electrical charge through the sample. The distance and width of electrodes can also be optimized for different conductivity measurement ranges to suit particular applications. It is also preferable that each of the electrodes 18 has a length (extending into the page in FIG. 1a) that exceeds the distance between the electrodes 18. Such a relationship tends to compensate for the fact that field lines spread out at sharp corners and ends of the electrodes 18 and current tends to follow the field lines. Long, narrow electrodes 18 are thus preferred to minimize these end effects.

Figure 1B:
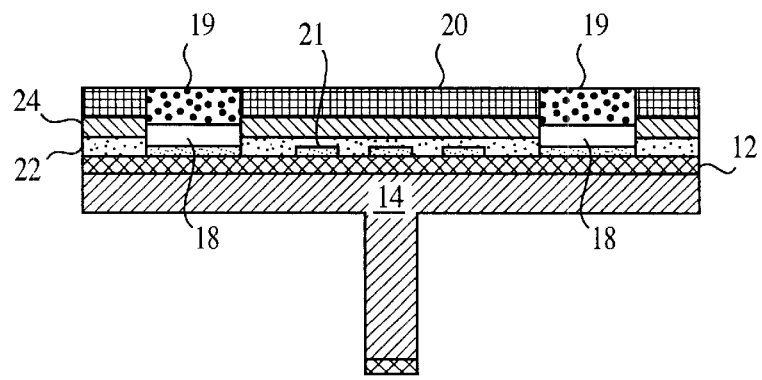
FIG. 1b is a cross-section view of the sensor tip of a preferred embodiment two-electrode sensor of the present invention including an integrated four-wire thin-film resistor and formed into a probe shape.

Since chemical reactions should be minimized during conductivity measurements, the preferred electrode 18 is made of a material that has a very high resistance to charge transfer that causes chemical reactions at the electrode/liquid interface, thus minimizing any conduction current. Nearly ideal polarized electrodes that inhibit conduction current are obtained when the electrodes 18 are made of platinum (Pt) or gold (Au). In FIG. 1a, the electrodes 18 are formed of Ni and are coated with a thin-film of Au to reduce the oxidation of the Ni further. In FIG. 1b, the Ni/Au films are coated with a black platinized (Pt-black) coating 19 to reduce the overall impedance across the electrode-solution interface by increasing the effective area for capacitive currents to occur. The effective surface area is increased hundreds of times after Pt-black electroplating. With impedance at the interface greatly reduced, measurement of the current is simplified. Pt-black also stabilizes the output signal. Without Pt-black 19, the output is much smaller and shows strong frequency dependence from 1 to 10 kHz. The signal suffers from drifting over time because of oxidation and reduction of the electrode and electrolyte, as well as fouling of the electrodes 18, even when the electrodes are formed of inert materials, i.e., Au or Pt. With Pt-black plating, the signal changes only 0.1% over several days, which may be at the limit of repeatability of the measurement electronics and does not show frequency dependence at frequencies greater than 1 kHz for a prototype device that has been tested. An additional passivation layer 20 is also shown in FIG. 1b, which is also used as the electroplating mold for the Pt-black 19.

The 4-electrode sensor acts to control the electrode by using current carrying electrodes and potential sensing electrodes. By having two sets of electrodes, the effect of the impedance of the current carrying electrodes is reduced in importance, since the potential sensing electrodes are used to determine the resistance of the solution. The current flow through the potential sensing electrodes is very small, since these are connected to a high-impedance measurement circuit, thus minimizing the effect of the potential sensing electrode impedance on the solution resistance measurements. In addition to improving measurement accuracy, 4-electrode sensors also greatly reduce the effect of fouling on the measurements, increasing the length of operation without significant degradation in the signal.

An integrated temperature sensor 21 is contained in the sensor 10, protected by an insulation layer 22, e.g., silicon nitride, also used to isolate the electrodes 18 from each other. As shown in FIGS. 1a and 1b, a second insulation layer 24 may also be added to further isolate the electrodes. The temperature sensor 21 is, for example, a thin-film resistor, preferably formed into a serpentine shape to produce significant resistance (hundreds to thousands of Ohms) while consuming a small area of the sensor tip. More generally, four types of temperature sensors might be used: thermal resistors, thermistors, thermocouples and junction-based thermometers.

The temperature sensor may aid accurate calculation of a conductivity measurement taken by the sensor 10. However, the sensor may be omitted if not necessary. The sensor 10 should possess a fairly linear temperature response. The resistance is suitably modeled as:

$$R_T = R_0(1+\alpha T)$$

where $\alpha$ is the temperature coefficient of resistance. Higher order terms are added where better accuracy is required over a wide temperature range. A high value of $\alpha$ is preferred. Generally, $\alpha$ increases with film thickness, however thicker films need a longer path length to get sufficient resistance for accurate resistance measurement. Metals, metal oxides and semiconductors, such as doped polysilicon, can be successfully used to form the temperature sensor, and depending on the application and fabrication method, may be the preferred materials. In FIG. 1a, the temperature sensor 21 is formed from Ni.

Self-heating of the temperature sensor is a concern when the sensor is made small. Resistance of the temperature sensor 21 generates heat that should be dissipated without appreciably increasing the temperature of the sample to be measured. Conduction through the substrate 14 is preferably minimized to reduce heat conduction to the ambient environment through the sensor 21 and to reduce the time constant due to the thermal mass. Preferably, the temperature sensor is located between the electrodes 18. In cases where there is a temperature gradient from one electrode 18 to another, locating the temperature sensor 21 between them provides an average value. This location also allows the sensor 10 to be fabricated easily. Higher current and thus higher temperature operation of the temperature sensor can be used to make fluid velocity measurements, like an anemometer, if desired.

The four-electrode sensor 18 of FIG. 1a is preferred for the accuracy of four-electrode conductivity measurements known in the art. Where less accuracy is required, a two-electrode sensor may be used. Such a sensor is shown in FIG. 1b, with like elements being labeled with the same reference numerals used in FIG. 1a.

FIGS. 2a to 2d are top views of four separate sensors of the invention. FIG. 2a illustrates a four-electrode sensor in which leads 26 extend from the electrodes 18 to bonding pads 28 that serve as electrical contacts to the sensor. The bonding pads 28 are formed on a wide end 30 of a substrate 14 while the electrodes are formed on a narrow tip portion 32. FIG. 2b shows a four electrode sensor including a four wire temperature sensor 21. FIG. 2c shows a simple two-electrode sensor. FIG. 2d shows a two-electrode sensor including a two wire temperature sensor 21 with an integrated measurement circuit 34.

Broader aspects of the invention may be modified to suit particular desired performance issues. The choices for particular practical implementations of the invention will affect the exact manner in which the device is fabricated. Some exemplary practical implementations are summarized prior to a discussion of general fabrication. The planar 2- and 4-electrode conductivity sensors may be combined with Pt-black to increase electrode area. The 2- and 4-electrode conductivity sensors may be combined with a temperature sensor, preferably but not necessarily in between the electrodes. Thick passivation layers may be made from at least one dielectric, and preferably two or more, which can include a polymer such as polyimide. The conductivity sensor can be shaped to form a probe, needle, or other shape, for multiple uses that include monitoring liquid streams or inserting into tubing or into tissue. The sensors can be fabricated in wafer form, and then separated into single pieces after most or all the fabrication steps are completed. The combination of substrate, conductivity electrodes (potentially with a temperature sensor), leads, potentially an electronic circuit, electrical connectors, and passivation layers when all the fabrication steps are complete creates a self-packaged sensor. The temperature sensor can also be used in heating mode to be used as an anemometer to measure fluid velocity. The electrodes can be over driven with current to heat in order to de-foul the surfaces. In addition, the polarized-electrodes can be combined with a reference non-polarized electrode, such as silver chloride on the back side, to give a measure of pH as well as conductivity. Selective ion permeability membranes can also be applied to the top of the probes to give the conductivity sensor ion selectivity, if desired. Therefore, a fully-integrated probe can measure conductivity, temperature, pH, and fluid velocity, provided the appropriate electrical circuit is used.

Several fabrication processes were developed to prototype integrated thin film liquid conductivity sensors of the invention. The overall fabrication technologies used are those used in the semiconductor and the microelectromechanical systems industries. The equipment and processes are known to those skilled in the art. Fabrication of the components on a microscale may be carried out using multiple depositions of conductive and passivating layers and multiple etchings to form the electrodes and pads/contacts. The choice of substrate composition, material purity, sensor film thickness, thermal mismatch among the substrate, metal film and passivation films, deposition method, deposition temperature, post deposition processing steps and heat treatment all may have considerable effect on the performance of the integrated sensor, as can be appreciated by those skilled in the art. Several different fabrication processes and material dimensions can achieve the same results. The following elucidates specific fabrication methods used to fabricate prototypes.

Prototype devices of the type shown in FIGS. 2a–2d were formed on a four-inch silicon wafer that served as substrate 14, which was coated on both sides with 10,000 angstroms (Å) of thermal dioxide ($SiO_2$) for dielectric layer 12. All succeeding layers were coated on the same (top) surface 12. The wafer was then coated by evaporation and/or sputtering with the first thin-film layer consisting of approximately 50 Å of titanium (Ti), 1000 Å of nickel (Ni) and another layer of 100 Å Ti to form both the temperature sensor 21, the first layer of electrodes 18, leads 26 and pads 28. Titanium is used as an adhesion promoter for the nickel layer on the thermal oxide layer 12 and for subsequent processes. Other materials such as chrome (Cr) or tungsten (W) can also be used for adhesion promotion. The Ti/Ni/Ti layer was then patterned with standard microfabrication techniques to form the base of electrodes 18, leads 26 and pads 28.

To prevent chemical reaction or conduction of currents from temperature sensor 21 and leads 26 through the solution, a first passivation layer of silicon nitride ($SiN_x$) is deposited in a thickness of approximately 5000 Å at 300° C. using a plasma-enhanced chemical vapor deposition process. $SiN_x$ is preferred over $SiO_x$ as a passivation material since water molecules diffuse into and hydrate with $SiO_x$, which may cause long term degradation of the operation of the sensor. Following deposition of passivation layer 22, a photoresist layer was added and then patterned with standard photolithography techniques. A low power fluorocarbon ($CF_4$) Reactive Ion Etching (RIE) process was employed to etch the $SiN_x$ down to the Ni metal layer to expose electrodes 18, leads 26 and pads 28. This RIE process slightly undercuts the $SiN_x$ layer to provide a shadow mask for evaporation, enabling the subsequent patterning of the ductile gold (Au) layer. The RIE process also removed the top Ti layer exposing Ni.

The wafer was then coated with 200 Å Cr, 2500 Å Au, 300 Å Cr using thermal evaporation to provide a nearly ideal polarized layer for electrode 18, once the 300 Å Cr layer is removed. Platinum or other polarized electrode material may also be used. The 300 Å top Cr layer is used to protect the Au during a subsequent RIE process. This Cr/Au/Cr layer is then patterned by a liftoff microfabrication method by removing the photoresist layer that underlies the Cr/Au/Cr everywhere except where the $SiN_x$ layer was removed and undercut with the $CF_4$ RIE process.

To insulate the leads 26 from contacting the liquid solution, a second passivation layer 24 of $SiN_x$ is deposited on the second thin film layer, and is preferably slightly thicker than the first passivation layer, from about 8,000 Å to about 12,000 Å. This passivation layer is patterned using photoresist and the $CF_4$ RIE process to open up the pads 28. To facilitate soldering of wires to the pads for the prototype, a 2000 Å copper layer was thermally evaporated on top of the Ni/Au layer and patterned with the liftoff technique. For an embodiment of the type shown in FIG. 1a, an additional photolithography and RIE process was used to remove the passivation layer 24 to expose electrodes 18. For an embodiment of the type shown in FIG. 1b, an additional protective passivation layer 20, is deposited and patterned before the electrodes 18 are exposed with RIE.

For a preferred embodiment, the electrodes 18 are plated with Pt-black 19 to increase the effective area of the electrodes. Due to the small size of the electrodes, the Pt-back coatings require a higher current density than is normally used in the prior art to form high surface area platinum. Plating of the Pt-black 19 to the Au electrode 18 surface was accomplished in a bath with 120 ml HPLC water, 5 g of chloroplatinic acid ($H_2PtCl_6 \cdot H_2O$), and 30 mg lead acetate ($Pb(CH_2COOH)_2 \cdot 3H_2O$) with a current density of from about 50 to 100 $mA/cm^2$ for 2–3 minutes. Lower current densities produce relatively smooth surfaces, and considerably higher current densities can lead to premature device failure, or overplating of the electrodes from the molds formed by passivation layers 24 and/or 20.

A protective layer, preferably plastic, may be deposited on the sensor tip 10 as an additional passivation layer 20. Many plastic polymers can be used, such as polyimide, polymethylmethacrylate (PMMA), photoactive epoxy (EPON or SU-8), paralyene, and aromatic thermosetting polyester. Polyimide is preferably used in one embodiment due to its tough mechanical properties to provide protection to the sensor. However, polyimide strongly absorbs water, which can be a detriment to long-term operation, whereas other polymers may not. Therefore, other polymers may be preferred for some applications, either alone or in conjunction with polyimide. The polyimide used for the prototypes was cured at about 350° C. or higher to harden.

Although the additional passivation layer 20 is not essential to the operation of the unit, it provides several advantages. Firstly, the additional layer adds a thickness to the total passivation layers, reducing the stray capacitance of the leads with the solution, thereby improving performance. Secondly, it can be used in fabrication as an etch mask to form the probe shape and recesses used for a reference electrode and/or to reduce the thermal mass of the sensor. Thirdly, it can be used as an electroplating mold, so that Pt-black may be confined within the footprint of the electrode area when Pt-black is used, and also allowing it to be several microns thick (the thickness of the passivation layers), without spilling over the footprint area. Fourthly, the polymer layer, if not removed after fabrication, provides a protective layer that acts to package the sensor for direct use.

This invention thus enables, in a preferred embodiment, the creation of very small free standing conductivity probes. Standard microfabrication processing technologies, such as wafer dicing with thin diamond saws, are not suitable to separate the probes, particularly those less than 1 mm wide, from the substrate on which they are made. To enable the fabrication of the probes on silicon substrates, as shown in FIGS. 2a–2d, reactive ion etching (RIE) is used to cut through both sides of the silicon wafer until the probe shape is fully defined and ready to be separated from the wafer. In addition, RIE can be used to thin the wafer from the recess 16 of FIG. 1a. Similarly, the T-structure shown in FIG. 1b can be formed by RIE. By incorporating the protective polymer layer described above, through-etching with RIE can be used as the final fabrication step. In addition to these benefits, very small side tabs (on the order of microns thick) patterned so that they are not etched during the shaping of the probe are utilized to hold the probe in place until all processing is completed. The probes, therefore, remain attached to the wafer until they are ready to be separated from the wafer, similar to tabs left in polymer injection molding of multiple parts. The finished probes are removed at the end by breaking the tabs. This fabrication technology allows microconductivity probes to be made with high yield and in high volume.

Additional fabrication technologies can also be utilized through this invention. For substrates made of silicon or other semiconductor materials used in electronic circuits, the signal processing circuits, such as the circuit 34 in FIG. 2d, can be directly integrated with the sensor. Preferably, silicon wafers can be used to form electrical circuits made from diodes, transistors, resistors, capacitors, etc. prior to or after the sensor is formed. The key to achieving the smallest dimensions (on the order of 10 $\mu$m) for a preferred embodiment is to reduce the stray capacitance of the leads by making them as small as possible. One method is to have the electronic circuits used to drive the electrodes and measure the currents and voltages co-located on the sensor probe, such as shown in FIG. 2d. In this manner, the overall size of the invention can be made smaller if desired. An additional benefit may be to reduce the overall cost of the conductivity system that employs the invention.

Another embodiment of this invention involves use of an insulative material, such as glass as the substrate, and the formation of sensors directly on top of the substrate. The fabrication methodologies for such substrates are essentially the same as described above, save perhaps for the shaping of the probes. Substrates made of glass can be shaped with metal (Cr/Au/Cr) or other suitable masks and etched in hydrofluoric acid glass etchant (buffered oxide etchant) to etch out the cavities and form probe shapes, if desired. The overall size of prototypes made from glass is larger than with silicon substrates, but artisans will appreciate the benefits of glass substrates, particularly if the smallest sizes are not required.

Conductivity sensors of the invention may also include electrodes not formed into a narrow tip. FIGS. 1a and 1b show preferred embodiment sensors formed into a probe shape with a narrow tip. The tip placement of electrodes 18 and temperatures sensors 21 in FIGS. 1a and 1b is convenient in applications where intrusive conductivity measurements are required, e.g., sampling fluid within a vessel through a vessel wall, but other configurations will be suitable for applications such as droplet measurement.

Many other integrated devices including conductivity sensors of the invention will be apparent to artisans. One example is shown in FIG. 3, which is the top view of an integrated device including an array of sixteen four-electrode conductivity sensors $C_1$–$C_{16}$. The sensors are packaged on a chip with a set of I/0 connectors 51, a driver circuit 52, measurement circuits 53, an amplifier circuit 54, and a 4-wire temperature sensor 55. The chip style embodiment of FIG. 3 might be used, for example, with a fluidic transport system which transports samples to and from the various conductivity sensors $C_1$–$C_{16}$.

Through the probes of the invention, small sample volumes are achieved in the design and fabrication of the sensor. Specific issues that previously prevented very small volumes (less than milliliter) from being accurately sampled are resolved by the invention. (i) For a conductivity sensor to accurately measure the conductivity of such small volumes from calibrations made with large volumes, the sensor itself needs to be about an order of magnitude smaller than the volume desired. (ii) The capacitance and resistance (giving rise to a complex impedance) across of the electrodes themselves preferably are controlled by maximizing the effective area of the electrodes, and/or by using dual sets of electrodes, one for the current and another high-impedance set of electrodes to measure the solution resistance, which is the desired quantity to be measured. (iii) The stray capacitance and resistance (impedance) in the overall circuit, which includes the leads and integrated circuit, need to be minimized, else the stray impedance will dominate the measurement, which is undesirable. (iv) To physically achieve the small size, the above discussed fabrication technologies include etching the sensor into the final size, using passivation layers as the etch masks, electroplating molds, and packaging of a sensor probe. This invention allows the conductivity sensors to be mass producible and easy to package. Therefore, even for applications that do not need small sample size, such as rinse cycle and water deionization sensors, these sensors can be made economically enough to allow their use in these applications. There is an additional benefit for these applications. Due to the small size of the electrodes, these sensors can be operated at very low currents and thus use very little power. Therefore, these sensors can be used in low-power applications, such as in battery-operated systems. Also, due to the small size of the electrodes that are fabricated onto a low thermal mass substrate, these sensors can be driven at relatively high electrical current densities in order to heat the electrodes well above ambient temperatures. These relatively high temperatures act to remove contaminants on the electrodes, thus de-fouling the electrode. Although the same can be done for prior art sensors, due to the small size of the invention, far lower currents are needed, allowing an automated de-fouling cycle at currents and voltages consistent with normal electronic circuits. Thus, a much larger number of applications can be served with this invention over the prior art.

While a particular embodiment of the present invention has been shown and described, it will be appreciated by those skilled in the art that changes and modifications may be made thereto without departing from the invention in its broader aspects and as set forth in the following claims.

What is claimed is:

1. A thin film liquid conductivity sensor, comprising:
    a substrate;
    a dielectric thin film on said substrate;
    at least two thin film electrodes formed on said dielectric thin film, said thin film electrodes being exposed for contact with a liquid environment;
    thin film electrode leads from said thin film electrodes;
    a dielectric layer separating said thin film electrodes;
    thin film electrode contacts to said leads for connecting said thin film electrodes to circuitry.

2. The sensor of claim 1, further comprising an integrated temperature sensor formed in said dielectric layer, sensor leads from said sensor and sensor contacts for connected said sensor leads to circuitry.

3. The sensor of claim 2, wherein said temperature sensor comprises a metal thin film formed into a serpentine shape.

4. The sensor of claim 1, wherein said thin film electrodes are formed of metal electroplated with Pt-black.

5. The sensor of claim 1, wherein said sensor includes four thin film electrodes.

6. The sensor of claim 1, wherein said substrate comprises a silicon substrate.

7. The sensor of claim 6, wherein said sensor is shaped into a probe and said thin film electrodes are formed at a tip of the probe.

8. The sensor of claim 7, wherein said substrate includes a cavity under the area of said tip.

9. The sensor according to claim 1, wherein said substrate comprises a membrane.

10. The sensor according to claim 1, wherein said sensor is shaped into a probe and said thin film electrodes are formed at a tip of the probe.

11. The sensor according to claim 10, further comprising a temperature sensor formed between said thin film electrodes.

12. A liquid conductivity sensor device at least partially impressible in an electrolyte solution, comprising:
    a substrate including a dielectric thin film;
    at least two thin film electrodes formed on said thin film, said thin film electrodes being exposed for contact with a liquid environment;
    thin film electrode leads from said thin film electrodes;
    a dielectric layer separating said thin film electrodes;
    an integrated temperature sensor within said dielectric layer and between said thin film electrodes;
    measurement circuitry on said substrate connected to said thin film electrode leads and said integrated temperature sensor.

13. The sensor device of claim 12, wherein said at least two thin film electrodes comprises at least four thin film electrodes.

14. The sensor of claim 12, wherein said substrate includes a thinned area.

15. The sensor device according to claim 9, wherein said at least two thin film electrodes and said thin film electrode leads form an element in an array of duplicate sets of thin film electrodes and leads, the sensor device further comprising input/output connections to said measurement circuitry.

16. The sensor according to claim 12, wherein said substrate comprises a membrane.

17. The sensor according to claim 12, wherein said sensor is shaped into a probe and said thin film electrodes are formed at a tip of the probe.

18. A thin film liquid conductivity sensor, comprising:
    a dielectric thin film formed on a substrate having a probe shape less than 1 mm wide and terminating in a narrower tip;
    at least two thin film electrodes formed on said dielectric thin film at said tip, said thin film electrodes being exposed for contact with a liquid environment;
    thin film electrode leads from said thin film electrodes;
    a dielectric layer separating said thin film electrodes;
    thin film electrode contacts to said leads for connecting said thin film electrodes to circuitry.

19. The sensor of claim 18, wherein said probe shape is less than 500 $\mu$m wide.

20. The sensor of claim 18, wherein said probe shape is approximately 10 $\mu$m wide.

21. The sensor of claim 18, further comprising an integrated temperature sensor within said dielectric layer and between said thin film electrodes.

* * * * *

UNITED STATES PATENT AND TRADEMARK OFFICE
CERTIFICATE OF CORRECTION

PATENT NO.     : 6,573,734 B2
DATED          : June 3, 2003
INVENTOR(S)    : He et al.

It is certified that error appears in the above-identified patent and that said Letters Patent is hereby corrected as shown below:

<u>Column 10,</u>
Line 30, delete "9" and insert -- 12 -- thereto.

Signed and Sealed this

Seventeenth Day of February, 2004

JON W. DUDAS
*Acting Director of the United States Patent and Trademark Office*